(12) United States Patent
Ohkura et al.

(10) Patent No.: US 6,825,359 B2
(45) Date of Patent: Nov. 30, 2004

(54) QUINOMETHANE COMPOUNDS

(75) Inventors: Kenichi Ohkura, Nagano (JP); Yoshihiro Ueno, Nagano (JP); Masami Kuroda, Kanagawa (JP); Nobuyuki Sekine, Kanagawa (JP)

(73) Assignee: Fuji Electric Imaging Device Co., Ltd., Nagano (JP)

( * ) Notice: Subject to any disclaimer, the term of this patent is extended or adjusted under 35 U.S.C. 154(b) by 137 days.

(21) Appl. No.: 10/357,504

(22) Filed: Feb. 4, 2003

(65) Prior Publication Data

US 2003/0195359 A1 Oct. 16, 2003

(30) Foreign Application Priority Data

Feb. 13, 2002 (JP) ........................................ 2002-035570

(51) Int. Cl.[7] .................... C07D 333/16; G03G 15/06
(52) U.S. Cl. ........................................ 549/78; 430/75
(58) Field of Search ............................ 549/78; 430/75

(56) References Cited

U.S. PATENT DOCUMENTS 6,034,089 A * 3/2000 Han et al. ............... 514/269
6,653,034 B2 * 11/2003 Inagaki et al. ........... 430/58.15

FOREIGN PATENT DOCUMENTS

| JP | 1-206349 | 8/1989 |
|---|---|---|
| JP | 1-230054 | 9/1989 |
| JP | 3-290666 | 12/1991 |
| JP | 04-338760 | 11/1992 |
| JP | 4-360148 | 12/1992 |
| JP | 5-092936 | 4/1993 |
| JP | 05-150481 | 6/1993 |
| JP | 5-279582 | 10/1993 |
| JP | 6-130688 | 5/1994 |
| JP | 07-179775 | 7/1995 |
| JP | 8-209023 | 8/1996 |
| JP | 8-278643 | 10/1996 |
| JP | 9-151157 | 6/1997 |
| JP | 9-281728 | 10/1997 |
| JP | 9-281729 | 10/1997 |
| JP | 10-73937 | 3/1998 |
| JP | 10-239874 | 9/1998 |
| JP | 2000-75520 | 3/2000 |
| JP | 2000-143607 | 5/2000 |
| JP | 2000-199979 | 7/2000 |
| JP | 2000-204083 | 7/2000 |
| JP | 2000-314969 | 11/2000 |
| JP | 2000-314970 | 11/2000 |
| JP | 2001-142239 | 5/2001 |
| JP | 2001-222122 | 8/2001 |
| JP | 2001-228637 | 8/2001 |
| JP | 2001-330972 | 11/2001 |
| JP | 2002-37755 | 2/2002 |

OTHER PUBLICATIONS

Tatsushi Kobayashi et al., "Development of Organic Electron Transport Materials", pp. 173–176, (1992).
Yasufumi Mizuta et al., Synthesis and Xerographic Properties of Novel Naphthoquinone, pp. 21–24, (1997).
Hideki Okada et al., Synthesis and Properties of a Novel Electron Transporting Compound, 3,3'–dialkyl–4,4'–bis-naphthylquinone (DBNQ), pp. 207–210, (1998).
Yasuhiro Yamaguchi, et al., Application of Unsymmetrical Diphenoquinone Derivatives to Xerography (1) Molecular Design of a Novel Class of Polymer–dispersible Electron–transport–active Compounds, pp. 266–273, (7.2. 1991).
Yuji Miyahara, Facile Synthesis of 2,5–Diacylthiophenes, pp. 1147–1151, (Sep. 1979).

\* cited by examiner

Primary Examiner—Deborah C. Lambkin

(57) ABSTRACT

Quinomethane compounds having a structure represented by the general formula (1):

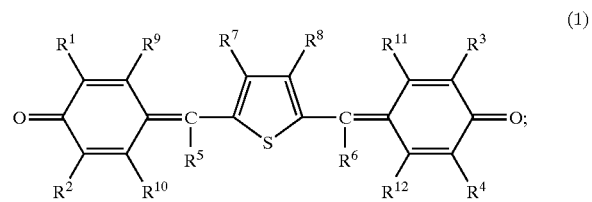

wherein $R^1$ to $R^4$ and $R^9$ to $R^{12}$ are the same or different and each represents a hydrogen atom, an alkyl group having 1 to 12 carbon atoms, a cyclic alkyl group, an aryl group, or an alkoxy group having 1 to 6 carbon atoms; $R^5$ and $R^6$ are the same or different and each represents an alkyl group having 1 to 12 carbon atoms, an aryl group, or a heterocyclic group; $R^7$ and $R^8$ each represents a hydrogen atom; and optional substituents are each a halogen atom, an alkyl group having 1 to 6 carbon atoms, an alkoxy group having 1 to 6 carbon atoms, an aryl group, or a heterocyclic group. Since these compounds transport electrons efficiently, they are useful in electrophotographic photoreceptors and/or organic electroluminescence applications.

5 Claims, 4 Drawing Sheets

QUINOMETHANE COMPOUNDS

CROSS-REFERENCE TO RELATED APPLICATIONS

This application claims the benefit of Japanese Application No. 2002-035570, filed Feb. 13, 2002, in the Japanese Patent Office, the disclosure of which is incorporated herein by reference.

BACKGROUND OF THE INVENTION

1. Field of the Invention

The present invention relates to quinomethane compounds, and in particular, to novel quinomethane compounds that are useful as an electron transport substance in an electrophotographic photoreceptor (hereinafter merely referred to as a 'photoreceptor'), an organic electroluminescence (EL) device or the like.

2. Description of the Related Art

In recent years, as electronic devices using an organic compound have been introduced, many organic electrophotographic photoreceptors that use an organic photoconductive material have been proposed and put into practical use, since organophotoconductive materials are non-polluting, low in cost, and the photoreceptor properties may be adjusted due to the degree of freedom of material selection.

The photosensitive layer of an organic electrophotographic photoreceptor predominantly comprises a layer in which an organic photoconductive material is dispersed in a resin, and many structures have been proposed, for example, a layered type structure in which a layer in which a charge generation material is dispersed in a resin (charge generation layer) and a layer in which a charge transport material is dispersed in a resin (charge transport layer) are laminated sequentially, and a single layer type structure comprising a single layer in which a charge generation material and a charge transport material are dispersed together in a resin.

Of the above, a functionally separated layered type photoreceptor in which a charge transport layer is laminated on top of a charge generation layer as the photosensitive layer has excellent photoreceptor properties and durability, and hence has been widely put into practical use. A hole transport material is generally used as the charge transport material in the charge transport layer provided in such a functionally separated layered type photoreceptor, and hence such a photoreceptor is used in an electrophotographic apparatus that operates with a negative charging process. However, the negative corona discharge used in the negative charging process is unstable compared with a positive corona discharge. Moreover, the amount of ozone generated is large, and hence, there have been problems of adverse effects on the photoreceptor and adverse effects on the usage environment. An organic electrophotographic photoreceptor that can be used with a positive charging process is effective for resolving these problems.

To make a photoreceptor having excellent durability as described above be suitable for a positive charging process and have high sensitivity, it is necessary to use a substance having an excellent electron transporting function. Many such substances and photoreceptors using these substances have been proposed. For example, in Japanese Patent Application Laid-open No. 1-206349, Japanese Patent Application Laid-open No. 4-360148, Journal of the Society of Electrophotography of Japan, Vol. 30, p266 to 273 (1991), Japanese Patent Application Laid-open No. 3-290666, Japanese Patent Application Laid-open No. 5-92936, Proceedings of the Pan-Pacific Imaging Conference/Japan Hardcopy '98, Jul. 15 to 17, 1998, J A Hall, Tokyo, Japan, p207 to 210, Japanese Patent Application Laid-open No. 9-151157, Papers from Japan Hardcopy '97, Jul. 9 to 11, 1997, J A Hall (Otemachi, Tokyo), p21 to 24, Japanese Patent Application Laid-open No. 5-279582, Japanese Patent Application Laid-open No. 7-179775, Papers from Japan Hardcopy '92, Jul. 6 to 8, 1992, J A Hall (Otemachi, Tokyo), p173 to 176, Japanese Patent Application Laid-open No. 10-73937, Japanese Patent Application Laid-open No. 4-338760, Japanese Patent Application Laid-open No. 1-230054, Japanese Patent Application Laid-open No. 8-278643, Japanese Patent Application Laid-open No. 9-190002, Japanese Patent Application Laid-open No. 9-190003, and Japanese Patent Application Laid-open No. 2001-222122, many electron transport substances and electrophotographic photoreceptors using such electron transport substances are proposed and disclosed, and have received attention. Moreover, in the case of a single layer type photosensitive layer, photoreceptors that use a combination of an electron transport substance and a hole transport substance as disclosed, for example, in Japanese Patent Application Laid-open No. 5-150481, Japanese Patent Application Laid-open No. 6-130688, Japanese Patent Application Laid-open No. 9-281728, Japanese Patent Application Laid-open No. 9-281729, and Japanese Patent Application Laid-open No. 10-239874, have received attention as having high sensitivity, and have been put into practical use in some cases.

Moreover, to obtain photoreceptors having better properties, the present inventors have also proposed photoreceptors that contain a substance having an electron transporting function (disclosed, for example, in Japanese Patent Application Laid-open No. 2000-75520, Japanese Patent Application Laid-open No. 2000-199979, Japanese Patent Application Laid-open No. 2000-143607, and Japanese Patent Application Laid-open No. 2001-142239).

Moreover, recently there are organic EL devices implemented as luminescent devices that use an organic photoconductive material and whose application to displays and the like is anticipated. With regard to these organic EL devices as well, many proposals have been made relating to improving the organic material, and practical application has been carried out in some cases.

The simplest structure of an organic EL device is a structure in which a luminescent layer containing a luminescent material that is an organic compound is sandwiched between electrodes; and by passing a current between the electrodes, electrons and holes are injected into the luminescent layer from the electrodes. Hence, excitons are formed in the luminescent layer, and then light is emitted when recombination occurs. Moreover, to inject electrons and holes efficiently into the luminescent layer from the electrodes, for example, a structure has also been proposed in which functional layers, namely a hole transport layer, a hole injection layer, an electron transport layer and an electron injection layer, are laminated together with the luminescent layer. Of these functional layers, an organic compound having an electron transporting function is used in the electron transport layer and the electron injection layer (see for example, Oyo Buturi, Vol. 70, No. 12 (2001), p1419 to 1425, 'Development Trends for High-Efficiency Organic EL Materials' (Omori)).

However, with diphenoquinone compounds and stilbenequinone compounds that are already known as substances having an electron transporting function when used in an electrophotographic photoreceptor, electrical properties such as residual potential and sensitivity are not sufficiently satisfactory. Hence, electron transport substances having better electrical properties have been hoped for. Moreover, in organic EL applications as well, there have been calls for high-performance electron transport materials that have higher brightness than conventionally, and moreover enable the luminous efficiency to be improved.

SUMMARY OF THE INVENTION

It is thus an aspect of the present invention to provide compounds that have an excellent electron transporting function and are thus useful in electrophotographic photoreceptor or organic EL applications.

Additional aspects and advantages of the invention will be set forth in part in the description which follows and, in part, will be obvious from the description, or may be learned by practice of the invention.

To attain aspects of the invention, a compound comprises a quinomethane compound having a structure represented by the below-mentioned general formula (1):

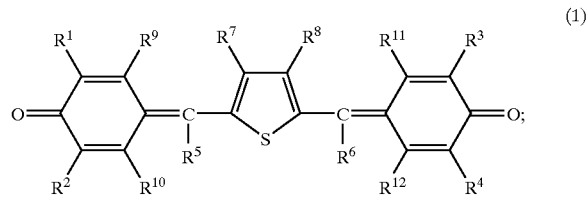

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an optionally substituted alkoxy group having 1 to 6 carbon atoms; $R^5$ and $R^6$ are the same or different and each represents an optionally substituted alkyl group having 1 to 12 carbon atoms, an optionally substituted aryl group, or an optionally substituted heterocyclic group; $R^7$ and $R^8$ each represents a hydrogen atom; and each of the optional substituents is a halogen atom, an alkyl group having 1 to 6 carbon atoms, an alkoxy group having 1 to 6 carbon atoms, an aryl group, or an optionally substituted heterocyclic group.

BRIEF DESCRIPTION OF THE DRAWINGS

These and other aspects and advantages of the invention will become apparent and more readily appreciated from the following description of the preferred embodiments, taken in conjunction with the accompanying drawings of which.

DETAILED DESCRIPTION OF THE EMBODIMENTS

Figure 1:
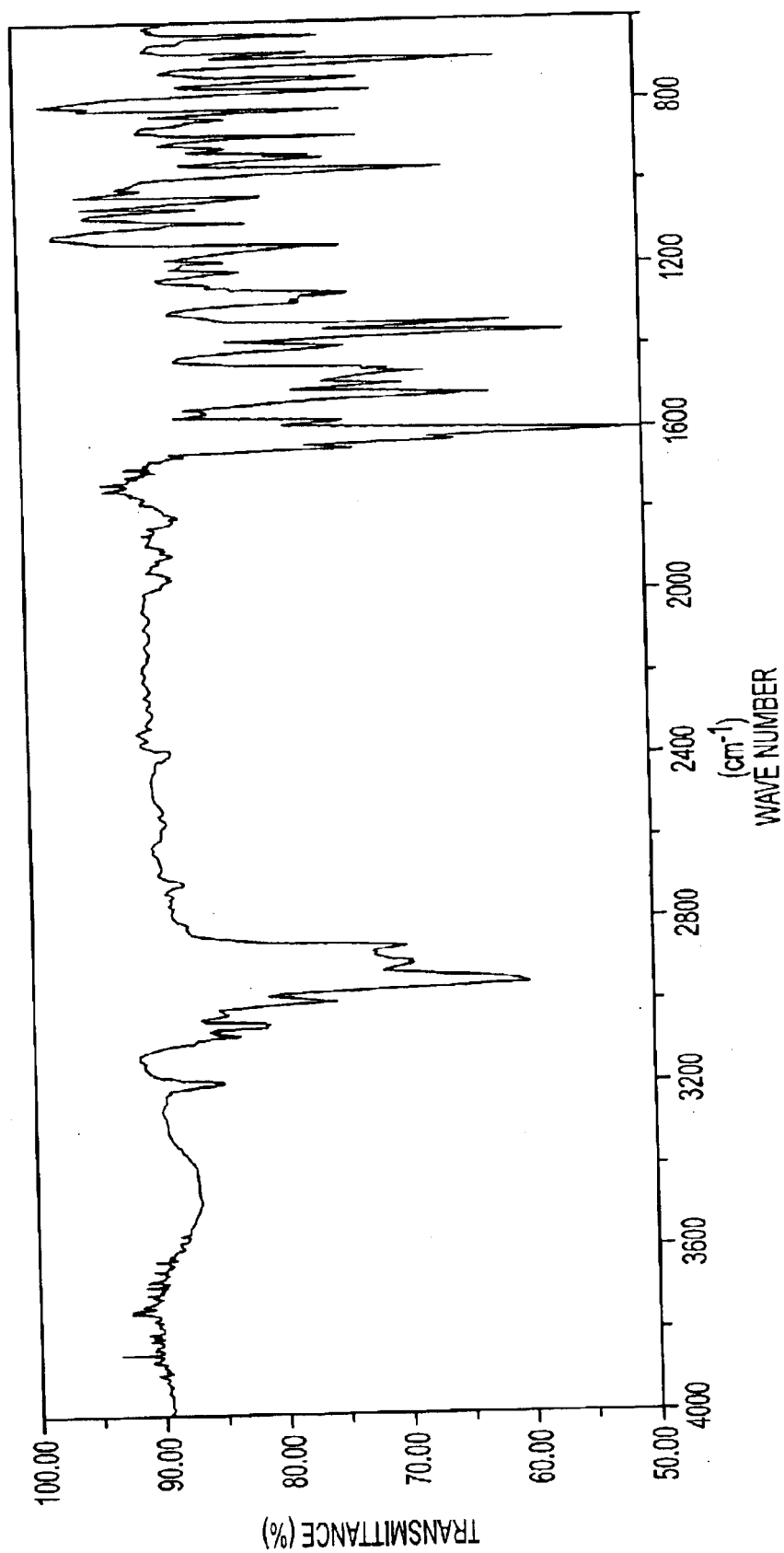
FIG. 1 is an IR spectrum of a compound according to an embodiment of the invention represented by structural formula 1-8.

Reference will now be made in detail to the present preferred embodiments of the present invention, examples of which are illustrated in the accompanying drawings, wherein like reference numerals refer to the like elements throughout. The embodiments are described below in order to explain the present invention by referring to the figures.

A compound of the present invention may be synthesized, for example, in accordance with the below-mentioned reaction formula (I). That is, as shown in the below-mentioned reaction formula (I), a compound represented by structural formula (1) may be synthesized by reacting the compound(s) represented by the below-mentioned structural formula (A) and/or structural formula (A') and the compound represented by the below-mentioned structural formula (B) together using a suitable organometallic reagent (e.g. n-butyl lithium), and then removing the protecting group (TMS: trimethylsilyl) to synthesize the compound represented by structural formula (C), and then carrying out condensation with loss of water using a suitable catalyst (e.g. p-toluenesulfonic acid). Note that in the below-mentioned reaction formula (I), TBAF represents tetrabutylammonium fluoride.

Reaction formula (I)

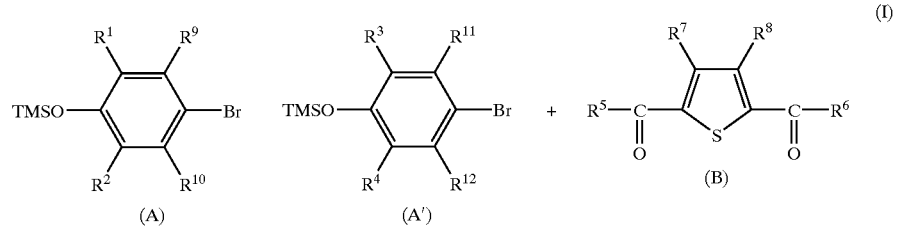

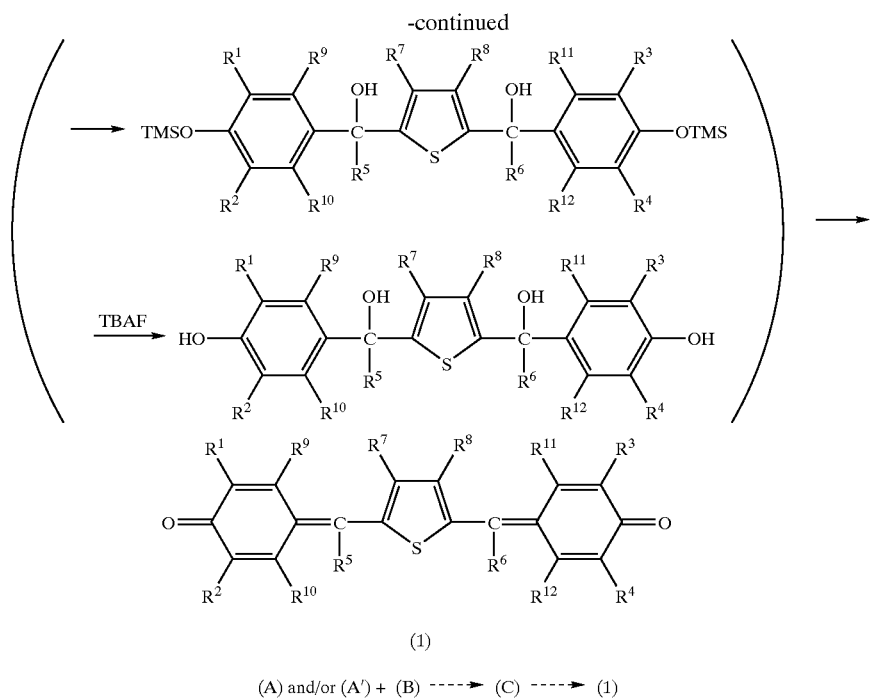
(1)
(A) and/or (A') + (B) ----▶ (C) ----▶ (1)
Specific examples of the compound represented by the above-mentioned general formula (1) are shown below, but there is no limitation to said compounds in the present invention. Note that the substituent '+' in the specific examples below represents a t-butyl group.
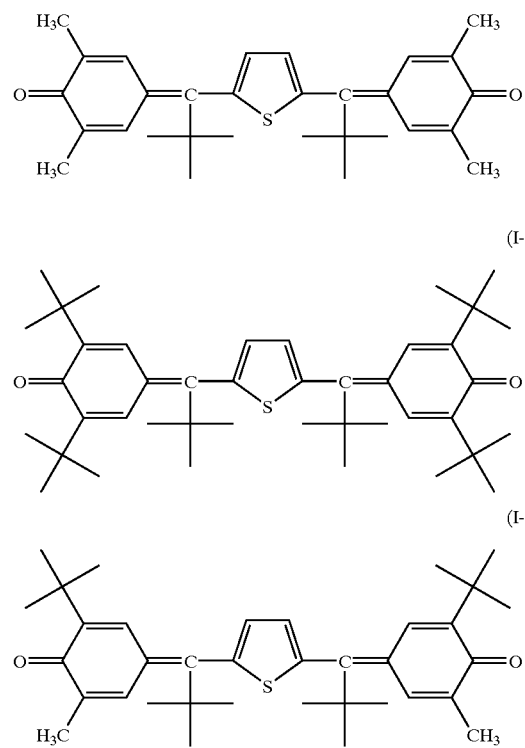
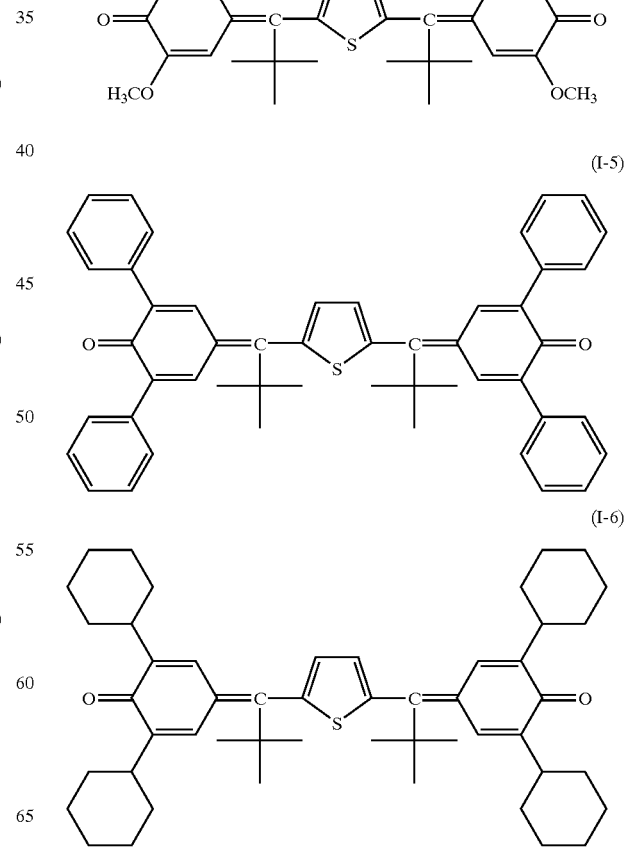

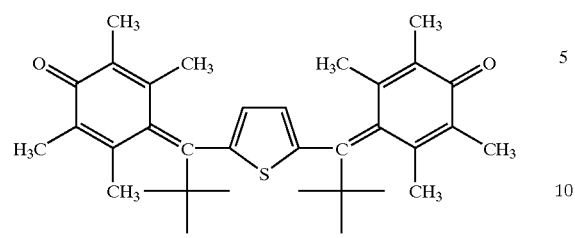
(I-7)
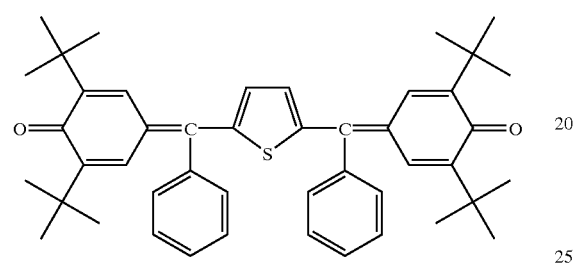
(I-8)
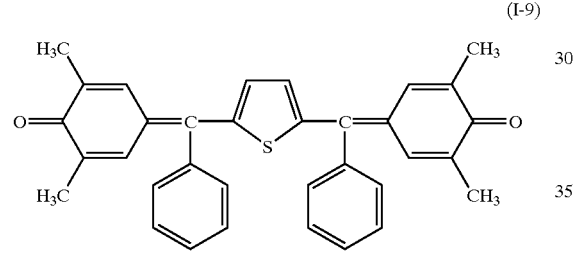
(I-9)
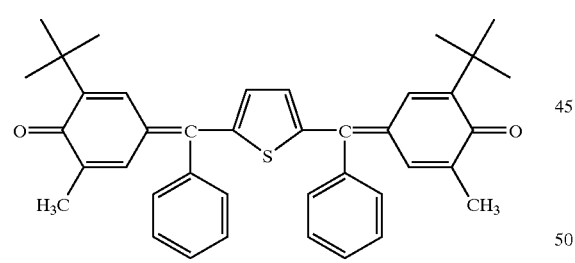
(I-10)
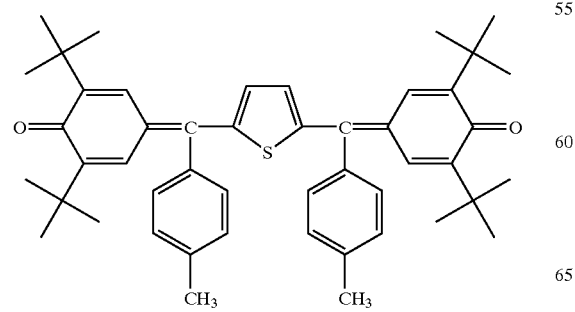
(I-11)
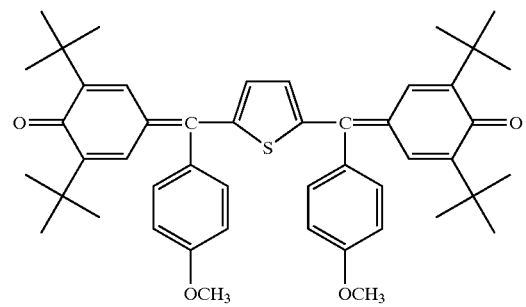
(I-12)
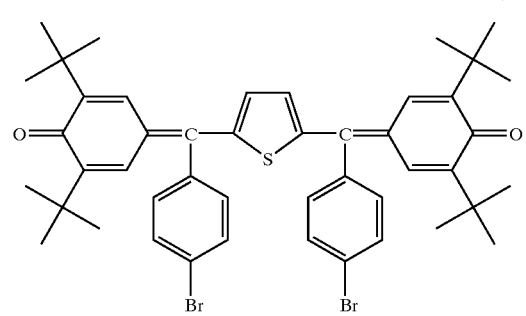
(I-13)
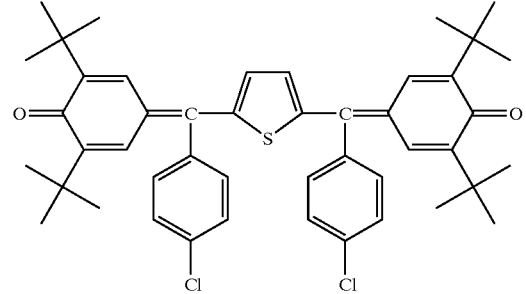
(I-14)
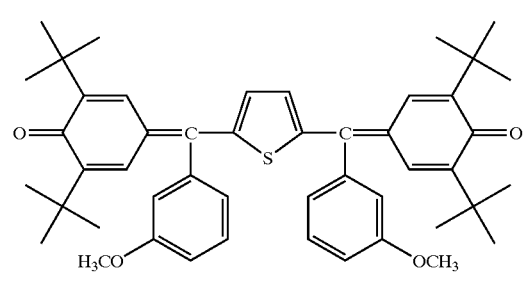
(I-15)
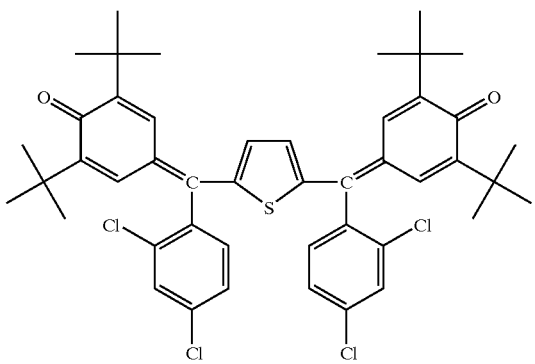
(I-16)

(I-17) 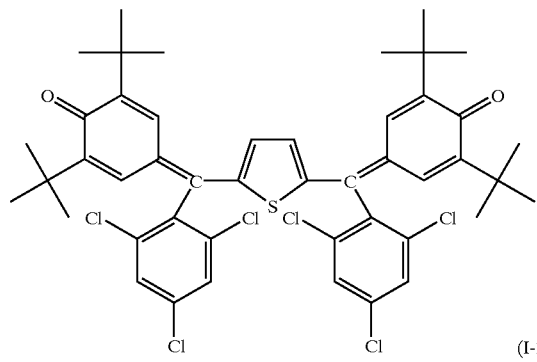
(I-18) 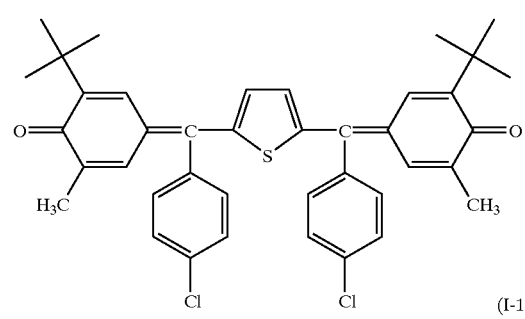
(I-19) 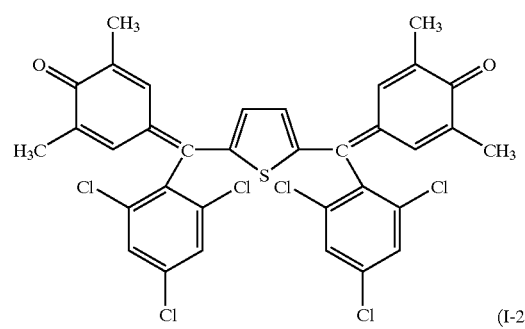
(I-20) 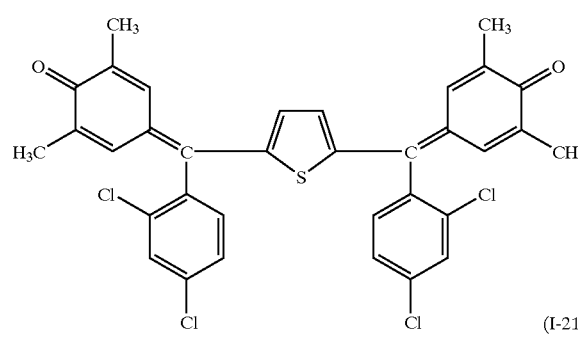
(I-21) 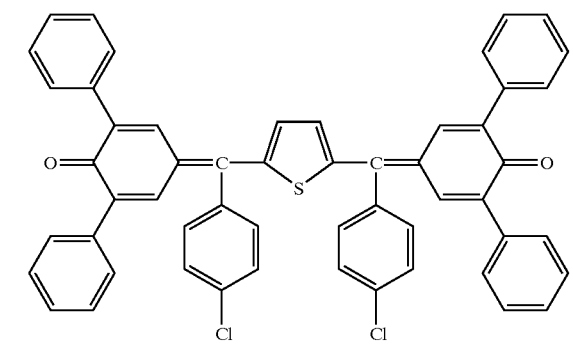
(I-22) 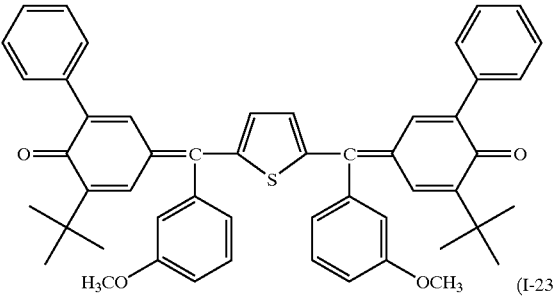
(I-23) 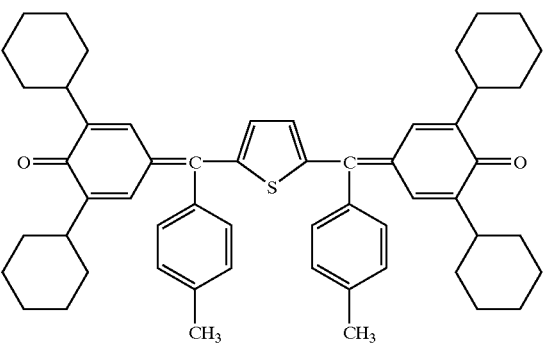
(I-24) 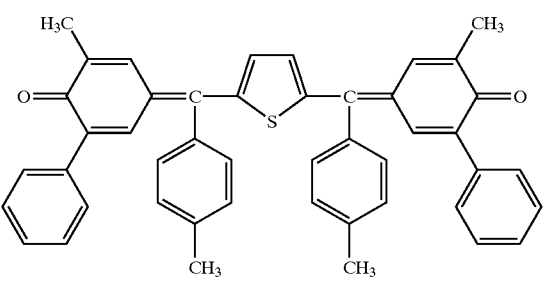
(I-25) 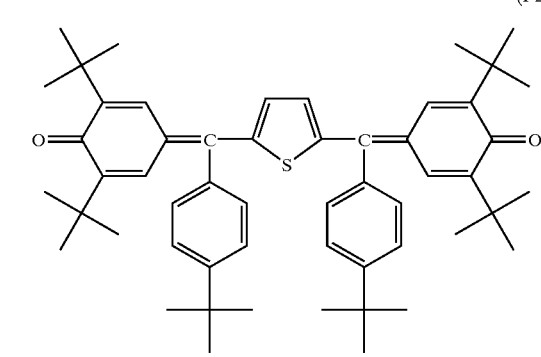
(I-26) 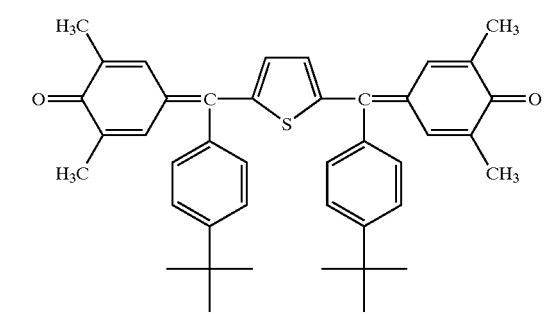

(I-27)
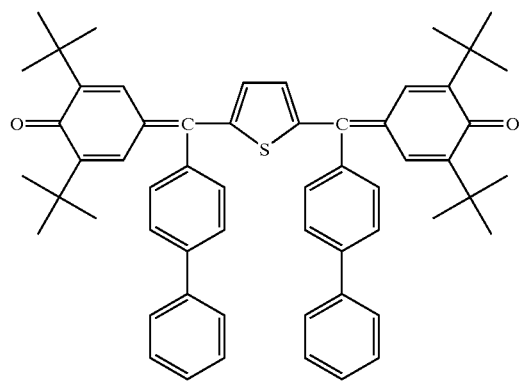
(I-31)
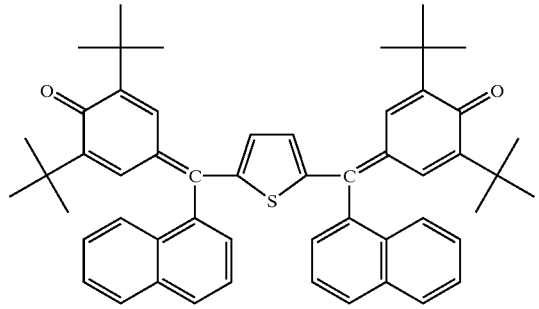
(I-28)
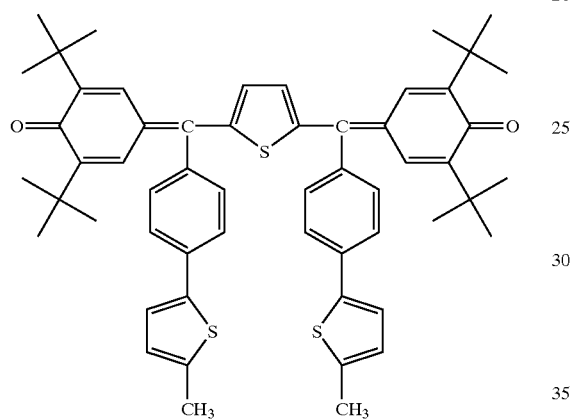
(I-32)
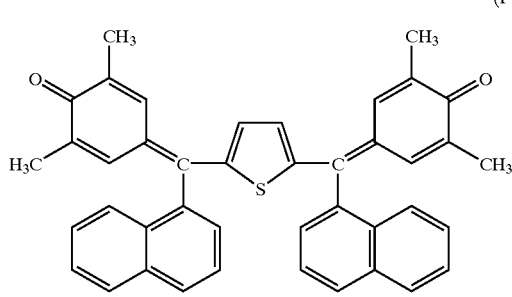
(I-29)
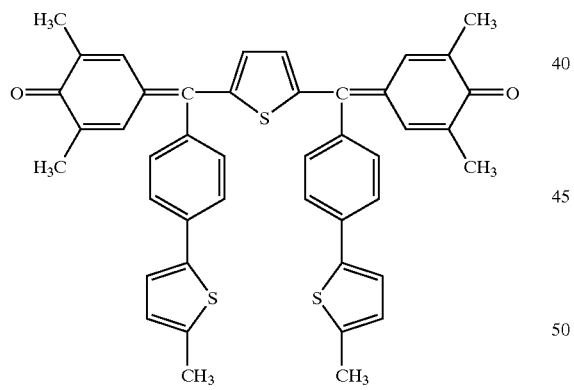
(I-33)
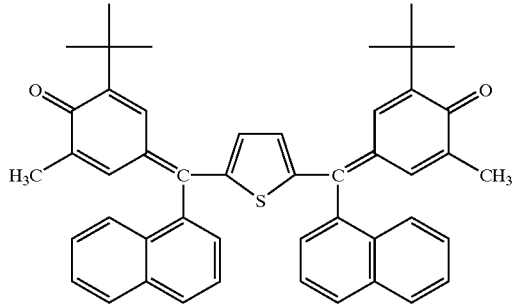
(I-30)
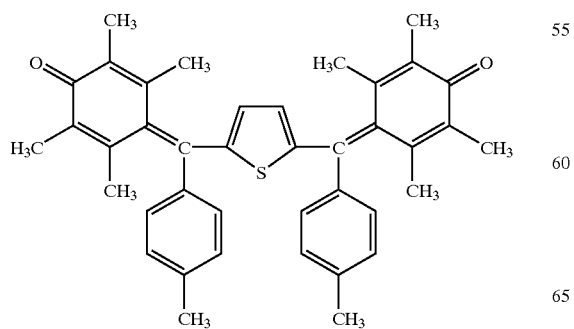
(I-34)
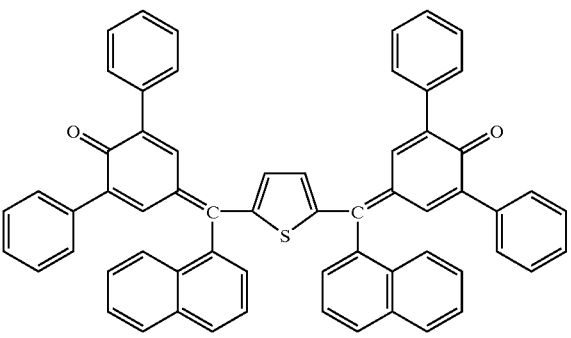

(I-35)
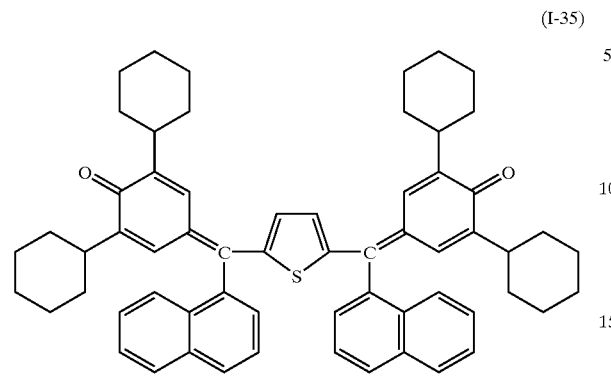
(I-36)
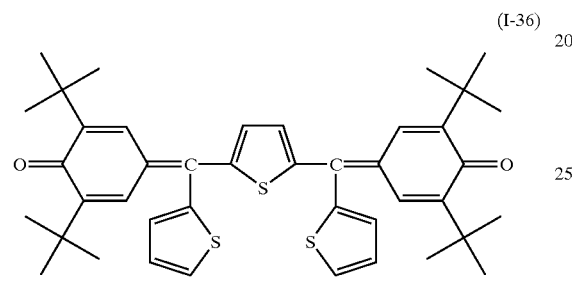
(I-37)
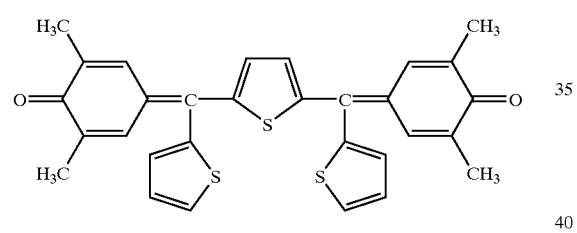
(I-38)
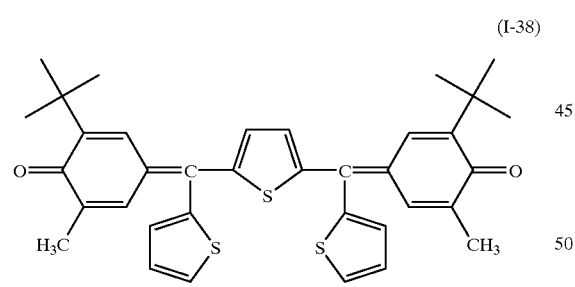
(I-39)
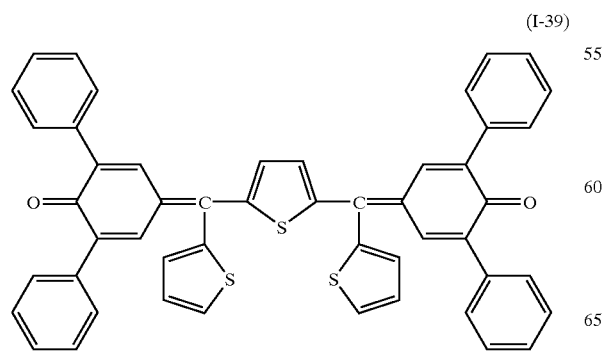
(I-40)
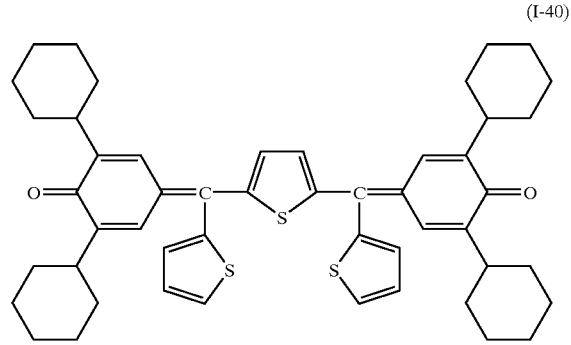
(I-41)
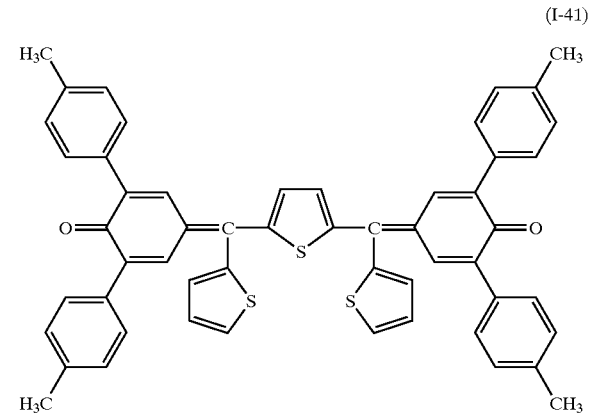
(I-42)
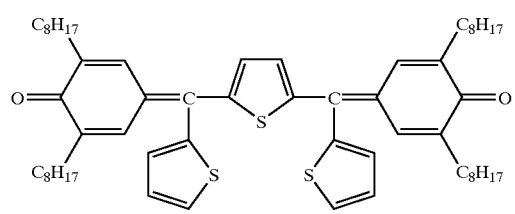
(I-43)
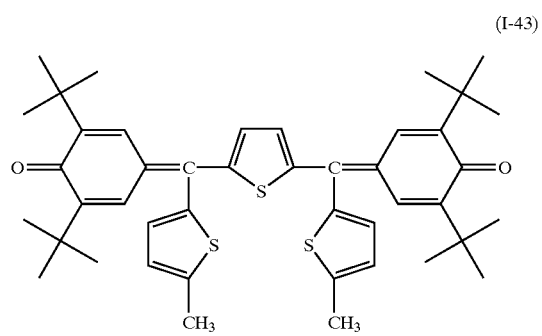

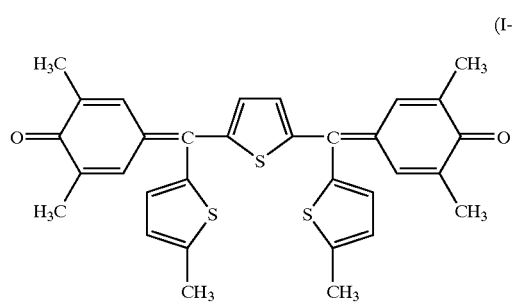
(I-44)

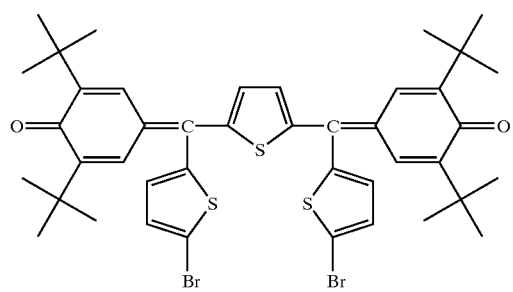
(I-45)

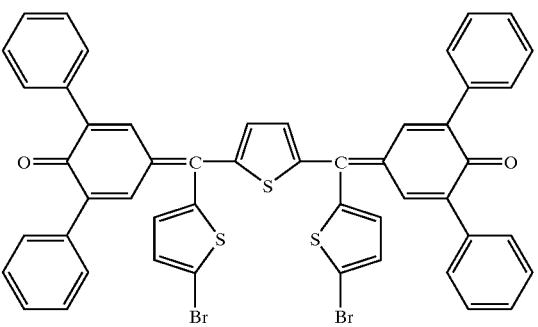
(I-46)

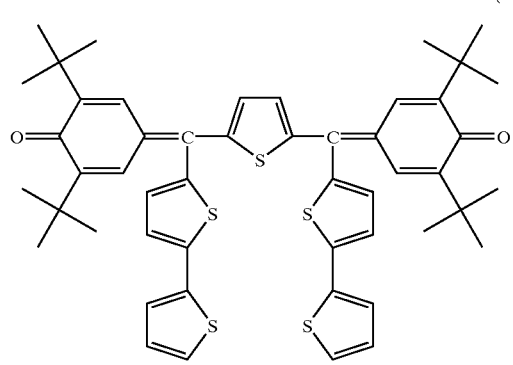
(I-47)

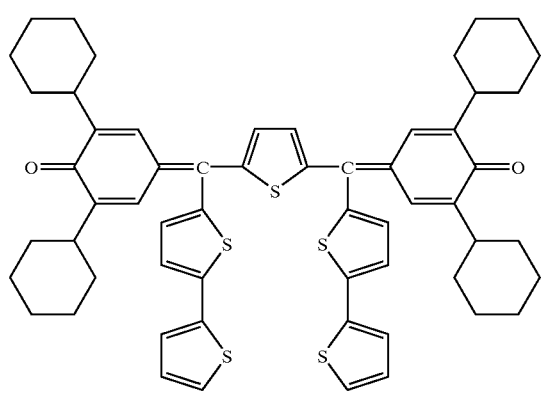
(I-48)

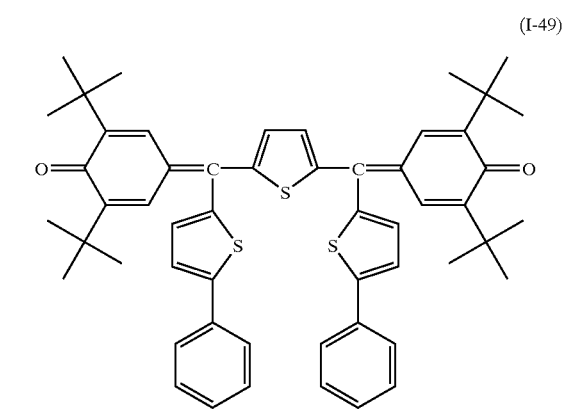
(I-49)

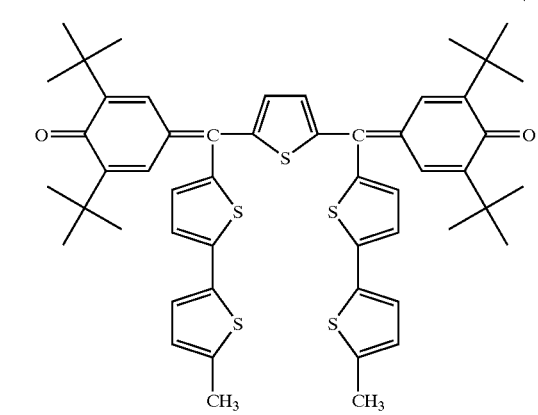
(I-50)

The quinomethane compounds of the present invention represented by above-mentioned general formula (1) have an excellent electron transporting ability, and are thus useful as a so-called electron transport material, and in particular can be suitably used as a material of a photosensitive layer of an electrophotographic photoreceptor, or a material of a functional layer such as an electron transport layer of an organic EL device.

Following is a description of embodiments of the present invention through examples.

SYNTHESIS EXAMPLE 1

Synthesis of Compound of Above-mentioned Specific Example 1-8

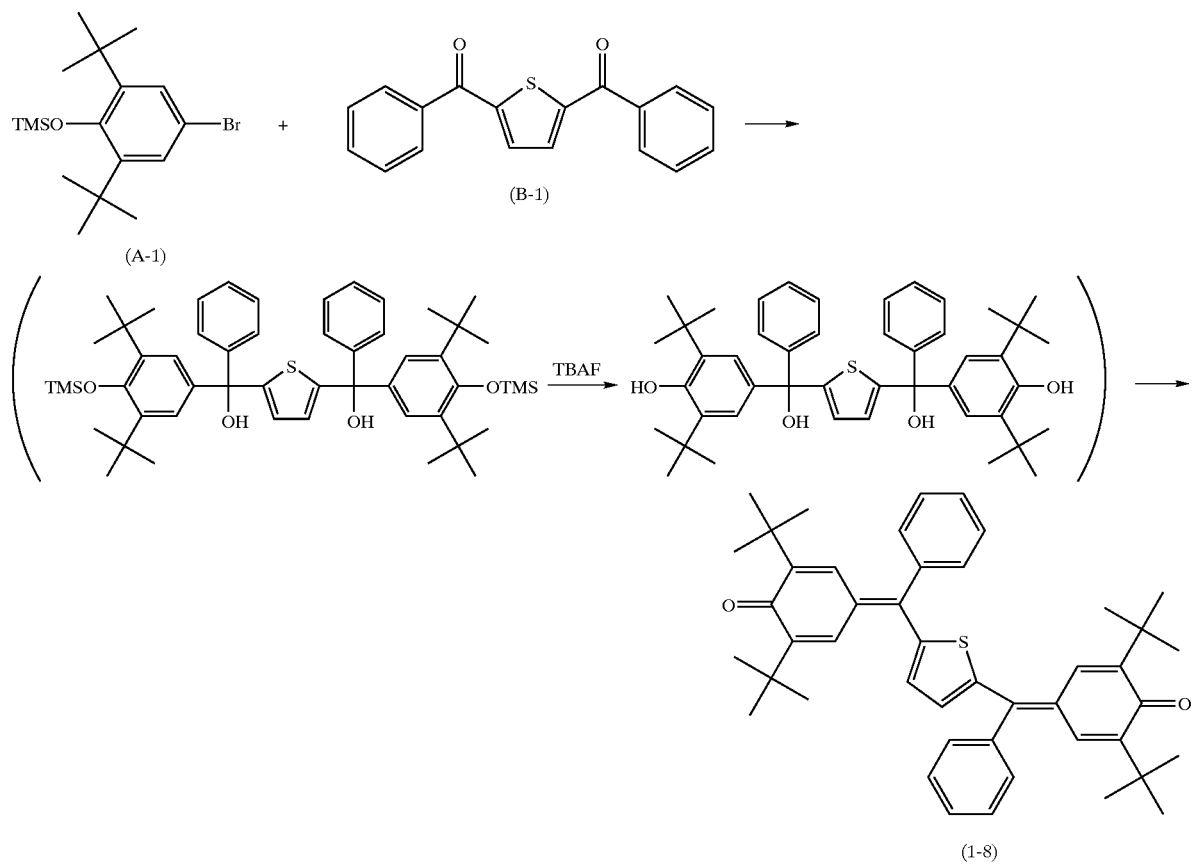

(Reaction formula I-1)

| (Starting materials and reagents) | |
|---|---|
| 4-bromo-2,6-di-t-butyl-1-benzene (A-1) | 50 mmol (17.9 g) |
| THF (tetrahydrofuran) | 100 ml |
| n-butyl lithium (1.6 M hexane solution) | 60 mmol (38 ml) |
| 2,5-dibenzoylthiophene (B-1) | 20 mmol (5.8 g) |
| THF (tetrahydrofuran) | 20 ml |
| Ammonium chloride aqueous solution | 10 ml |
| Tetrabutylammonium fluoride (TBAF) (1.0 M THF solution) | 50 mmol (26.1 g) |
| p-toluenesulfonic acid monohydrate (p-TsOH) | Small amount |
| Toluene | 100 ml |

(Method)

(1) The compound A-1 was weighed out into a 3-mouth flask, and THF (100 ml) was added.

(2) The n-butyl lithium was instilled in over 30 minutes under an $N_2$ atmosphere at −78° C. (dry ice—ethanol bath), and stirring was carried out for 30 minutes. A THF solution (20 ml) of the compound B-1 was then instilled in over 30 minutes under the same conditions, and stirring was carried out for 3 hours.

(3) Approximately 10 ml of saturated ammonium chloride aqueous solution was added, thus carrying out hydrolysis.

(4) The TBAF (50 ml) was added at 0° C. (ice bath), and stirring was carried out for 3 minutes.

(5) The reaction solution obtained was poured into ice water, and stirring was carried out.

(6) Extraction was carried out using dichloromethane, and then concentration was carried out.

(7) The solid component was dissolved in toluene (100 ml), a small amount of p-TsOH was added, and heating and refluxing were carried out for 2 hours.

(8) After the reaction had finished, concentration was carried out.

(9) The solid component was filtered off, and after washing with hexane, recrystallization was carried out using chloroform and ethanol.

Figure 2A:
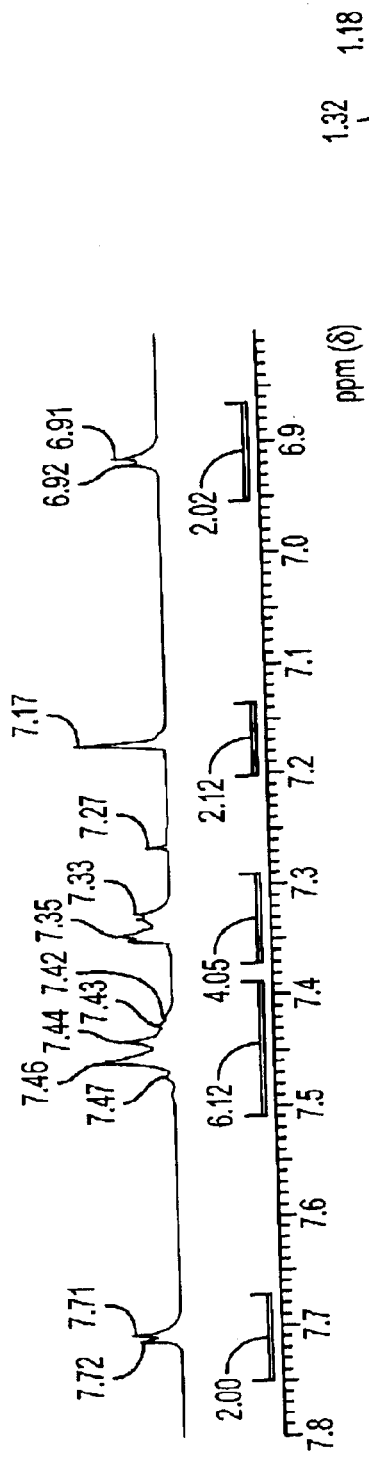
FIGS. 2A–2B are a $^1$H-NMR spectrum of the compound according to an embodiment of the invention, represented by structural formula 1-8.
Figure 2B:
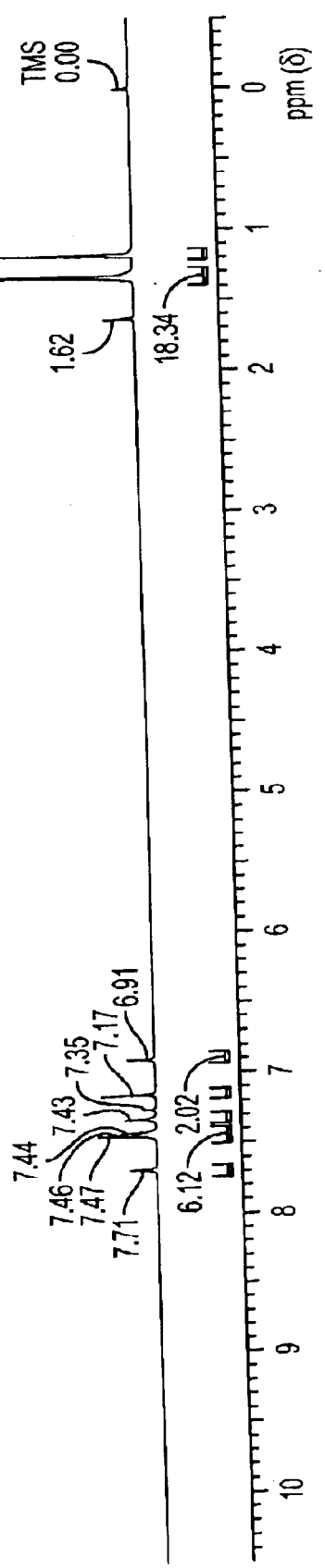

As a result of the above, the compound represented by above-mentioned formula 1-8 was obtained. The yield was 8.0 g (59.8%), and the MS was m/z 669 ($M^+$). The IR spectrum of the compound of this specific example 1-8 is shown in FIG. 1, and the $^1$H-NMR spectrum is shown in FIGS. 2A–2B.

SYNTHESIS EXAMPLE 2

Synthesis of Compound of the Above-mentioned Specific Example 1-36

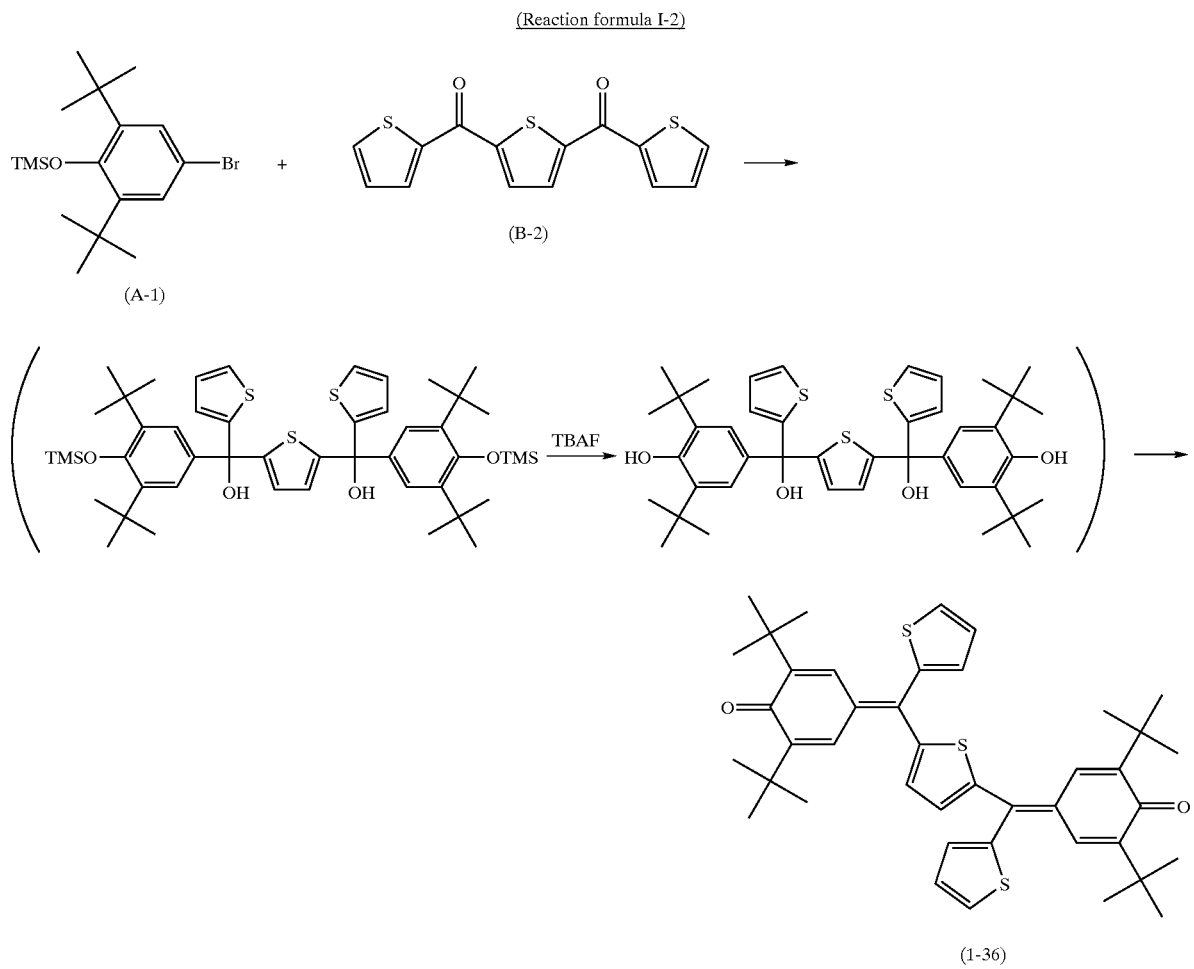

(Reaction formula I-2)

(1-36)

Figure 3:
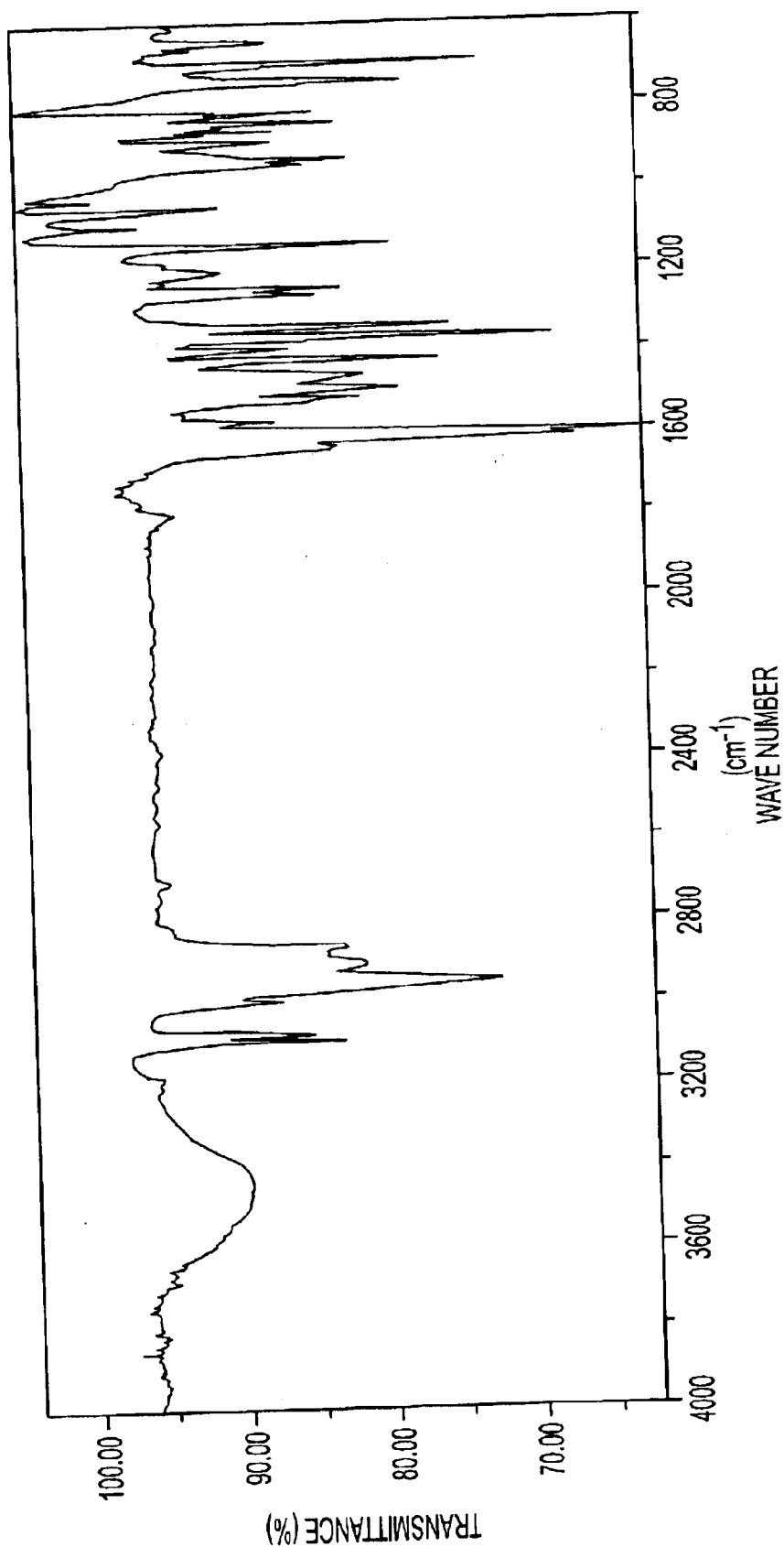
FIG. 3 is an IR spectrum of a compound according to an embodiment of the invention, represented by structural formula 1-36.
Figure 4A:
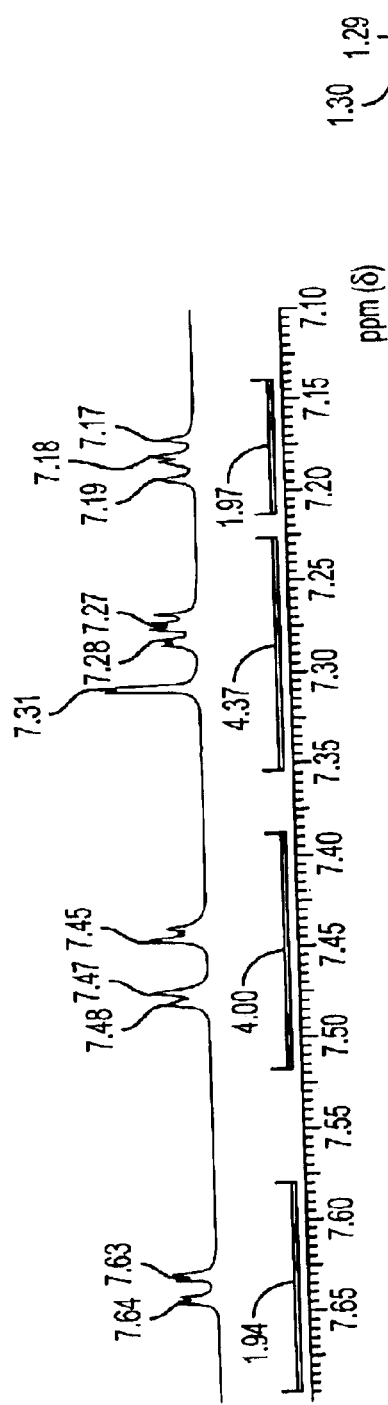
FIGS. 4A–4B are a $^1$H-NMR spectrum of the compound according to an embodiment of the invention, represented by structural formula 1-36.
Figure 4B:
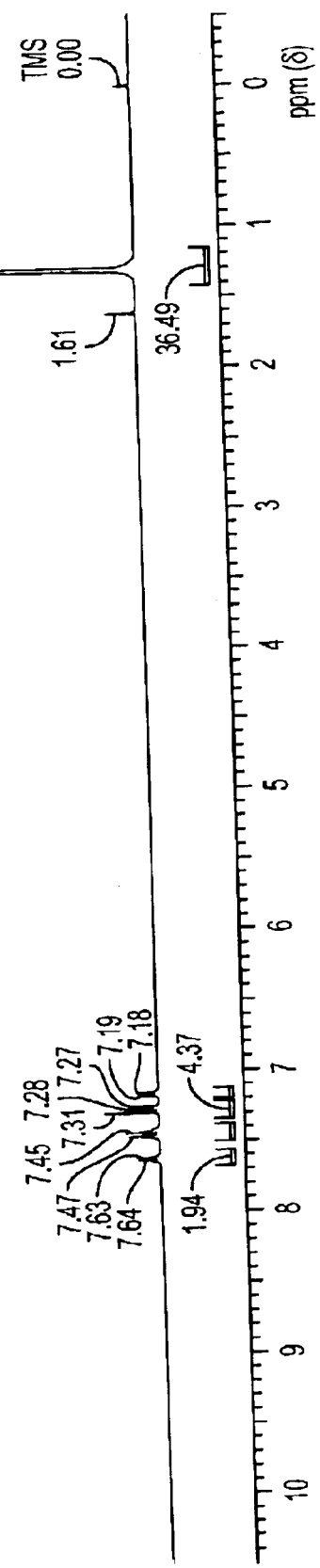

The same method was carried out as in Synthesis Example 1, except that the 20 mmol (5.8 g) of 2,5-dibenzoylthiophene (B-1) of Synthesis Example 1 was replaced with 20 mmol (6.1 g) of 2,5-dithenoylthiophene (B-2), whereby the compound represented by above-mentioned formula 1-36 was obtained. The yield was 4.9 g (36.0%), and the MS was m/z 681 (M+). The IR spectrum of the compound of this specific example 1–36 is shown in FIG. 3, and the 1H-NMR spectrum is shown in FIGS. 4A–4B.

Note that 4-bromo-2,6-di-tert-butyl-1-benzene (above-mentioned formula A-1) may be synthesized, for example, using the publicly known method disclosed in Japanese Patent Application Laid-open No. 2001-222122, and 2,5-dibenzoylthiophene (above-mentioned formula B-1) and 2,5-dithenoylthiophene (above-mentioned formula B-2) may be synthesized using the method disclosed in Y. Miyahara, J. Heterocyclic Chem., 1979, 16, 1147–1151.

Photoreceptor Applied Example 1

A plate-shaped photoreceptor for evaluating electrical properties, and a drum-shaped photoreceptor (30 mm diameter) for evaluating printing were each produced.

An undercoat layer solution of the below-mentioned composition was applied by dip coating onto each of an aluminum plate and an aluminum tube, and drying was carried out for 60 minutes at 100° C., thus forming an undercoat layer of thickness 0.3 µm. Note that in the following 'parts' means parts by weight.

| | |
|---|---|
| Soluble nylon (AMILAN ™ CM8000; made by Toray Industries, Inc.) | 3 parts |
| Methanol/methylene chloride mixed solvent (5/5) | 97 parts |

Next, a single layer type photosensitive layer dispersion of the below-mentioned composition was applied on by dip coating, and drying was carried out for 60 minutes at 100° C., thus forming a single layer type photosensitive layer of thickness 25 µm.

| | | |
|---|---|---|
| Charge generation substance: X-type non-metal phthalocyanine | | 0.3 parts |
| Hole transport substance: Styryl compound represented by below-mentioned structural formula HT1. | | 7 parts |

(HT1)

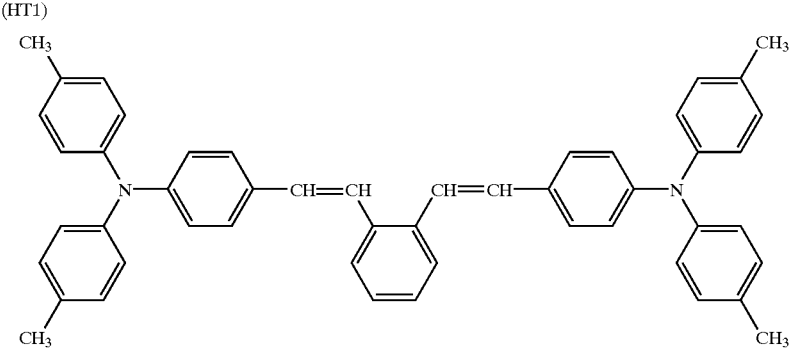

| | |
|---|---|
| Electron transport substance: Compound represented by above-mentioned formula 1-8 | 3 parts |
| Antioxidant: 3,5-di-tert-4-hydroxytoluene (BHT) (made by Tokyo Kasei Kohyo Co., Ltd.) | 1 part |
| Silicone oil: KF-50 (made by Shin Etsu Chemical Co., Ltd.) | 0.01 parts |
| Binder resin: Bisphenol Z-type polycarbonate resin (PANLITE ™ TS2020; made by Teijin Chemicals, Ltd.) | 10 parts |
| Methylene chloride | 100 parts |

By carrying out the above, electrophotographic photoreceptors were produced.

Photoreceptor Applied Example 2

Photoreceptors were produced as in Photoreceptor Applied Example 1, except that, out of the composition of the photosensitive layer dispersion used in Photoreceptor Applied Example 1, the 3 parts of the electron transport substance represented by above-mentioned formula 1-8 were replaced with 3 parts of the electron transport substance represented by above-mentioned formula 1-36 that was synthesized in Synthesis Example 2.

Evaluation of Photoreceptor Applied Examples 1 and 2

As the evaluation of electrical properties, using each of the plate-shaped photoreceptors, evaluation was carried out using an electrostatic copying paper testing apparatus EPA-8100 made by Kawaguchi Electric Works Co., Ltd.

Under an environment of a temperature of 23° C. and a humidity of 45%, charging was carried out in a dark place such that the surface potential became approximately +600 V, and then the retention rate of the surface potential during a time period of 5 seconds until exposure with light was carried out was calculated from the following equation.

Retention rate $V_{k5}(\%) = (V_5/V_0) \times 100$ $V_0$: Surface potential immediately after charging
$V_5$: Surface potential after 5 seconds (when exposure with light commenced)

Next, the surface potential was similarly raised to +600 V, and exposure was carried out for 5 seconds with 1.0 µW/cm² monochromatic light of wavelength 780 nm that was produced from halogen lamp light using a filter; the exposure required for the surface potential to be halved (to +300 V) was obtained as the sensitivity $E_{1/2}$ (µJ/cm²), and the surface potential after the 5 seconds of exposure was obtained as the residual potential $V_r$ (V).

The evaluation results are shown in Table 1 below.

| | Retention rate $V_{k5}$ (%) | Sensitivity $E_{1/2}$ (µJ/cm²) | Residual potential $V_r$ (V) |
|---|---|---|---|
| Photoreceptor Applied Example 1 | 84.3 | 0.36 | 48 |
| Photoreceptor Applied Example 2 | 81.2 | 0.39 | 51 |

Moreover, as an evaluation of the durability upon actual printing, each drum-shaped photoreceptor was installed in an HL-1240 laser printer made by Brother Industries, Ltd., and a solid black image, a solid white image and a half-tone image were printed under an environment of a temperature of 22° C. and a humidity of 44%. An image of printing proportion approximately 5% was then printed 5000 times, and then a solid black image, a solid white image and a half-tone image were printed once again, and the images after printing 5000 times were evaluated.

The results were that for Photoreceptor Applied Examples 1 and 2, good images were obtained for both the initial images and the images after printing 5000 times.

As described above, according to embodiments of the present invention, a compound having an excellent electron transporting ability can be obtained; by using said compound in an electronic device that uses an organic compound such as an electrophotographic photoreceptor or an organic EL device, properties such as electrical properties and luminous efficiency can be improved. For example, the present invention may be utilized in a backlighting unit, an electroluminescent wire, an electroluminescent display device, etc.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A quinomethane compound having a structure represented by the general formula (1):

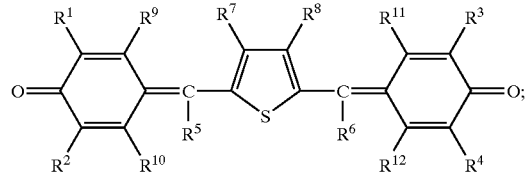

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an optionally substituted alkoxy group having 1 to 6 carbon atoms; $R^5$ and $R^6$ are the same or different and each represents an optionally substituted alkyl group having 1 to 12 carbon atoms, an optionally substituted aryl group, or an optionally substituted heterocyclic group; $R^7$ and $R^8$ each represents a hydrogen atom; and each of the optional substituents is a halogen atom, an alkyl group having 1 to 6 carbon atoms, an alkoxy group having 1 to 6 carbon atoms, an aryl group, or an optionally substituted heterocyclic group.

2. The quinomethane compound of claim 1, wherein the quinomethane compound is embedded in fibers between two electrodes and the quinomethane compound is illuminated via application of a voltage across the two electrodes.

3. A quinomethane compound for a backlighting unit comprising a cathode and an anode, having the quinomethane compound layered therebetween, the quinomethane compound comprising:

a structure represented by the general formula (1):

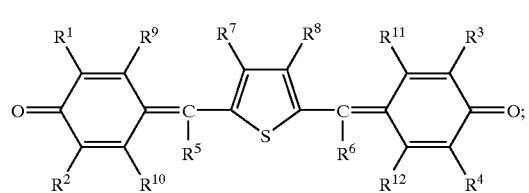

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an optionally substituted alkoxy group having 1 to 6 carbon atoms; $R^5$ and $R^6$ are the same or different and each represents an optionally substituted alkyl group having 1 to 12 carbon atoms, an optionally substituted aryl group, or an optionally substituted heterocyclic group; $R^7$ and $R^8$ each represents a hydrogen atom; and each of the optional substituents is a halogen atom, an alkyl group having 1 to 6 carbon atoms, an alkoxy group having 1 to 6 carbon atoms, an aryl group, or an optionally substituted heterocyclic group, and wherein, upon application of a voltage, the quinomethane compound electroluminesces to provide electroluminescent backlighting.

4. A quinomethane compound for an electroluminescent wire having a photosensitive coating on the wire, wherein said photosensitive coating comprises the quinomethane compound, the quinomethane compound comprising:

a structure represented by the general formula (1):

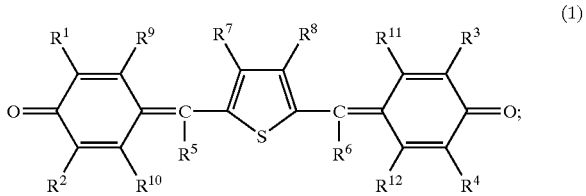

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an optionally substituted alkoxy group having 1 to 6 carbon atoms; $R^5$ and $R^6$ are the same or different and each represents an optionally substituted alkyl group having 1 to 12 carbon atoms, an optionally substituted aryl group, or an optionally substituted heterocyclic group; $R^7$ and $R^8$ each represents a hydrogen atom; and each of the optional substituents is a halogen atom, an alkyl group having 1 to 6 carbon atoms, an alkoxy group having 1 to 6 carbon atoms, an aryl group, or an optionally substituted heterocyclic group, and wherein, when a voltage is applied across the wire, the quinomethane compound electroluminesces.

5. A quinomethane compound for an electroluminescent display device of a type which comprises a matrix electrode structure comprising a plurality of scanning electrodes and a plurality of data electrodes and an organic layer having a luminescent region and located between the scanning electrodes and the data electrodes, wherein the organic layer comprises the quinomethane compound, the quinomethane compound comprising:

a structure represented by the general formula (1):

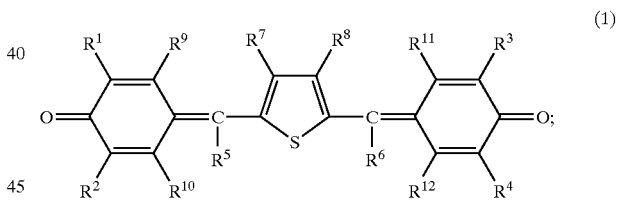

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an optionally substituted alkoxy group having 1 to 6 carbon atoms; $R^5$ and $R^6$ are the same or different and each represents an optionally substituted alkyl group having 1 to 12 carbon atoms, an optionally substituted aryl group, or an optionally substituted heterocyclic group; $R^7$ and $R^8$ each represents a hydrogen atom; and each of the optional substituents is a halogen atom, an alkyl group having 1 to 6 carbon atoms, an alkoxy group having 1 to 6 carbon atoms, an aryl group, or an optionally substituted heterocyclic group, and wherein, when voltage is applied sequentially across the scanning and data electrodes in a predetermined fashion, preselected portions of the organic layer electroluminesce to form a display.

* * * * *